(12) United States Patent
Roncal Martínez et al.

(10) Patent No.: US 11,111,474 B2
(45) Date of Patent: Sep. 7, 2021

(54) BACTERIAL STRAIN PRODUCING 2,3-BUTANEDIOL AND OTHER METABOLITES

(71) Applicant: FUNDACION TECNALIA RESEARCH & INNOVATION, Donostia-San Sebastián (ES)

(72) Inventors: Tomás Roncal Martínez, Donostia-San Sebastián (ES); Susana Caballero Román, Donostia-San Sebastián (ES); María Del Mar Díaz De Guereñu Zabarte, Donostia-San Sebastián (ES); Inés Rincón Arroyo, Donostia-San Sebastián (ES); Soraya Prieto Fernández, Miñano (ES); José Ramón Ochoa Gómez, Miñano (ES)

(73) Assignee: FUNDACION TECNALIA RESEARCH & INNOVATION, Donostia-San Sebastián (ES)

( * ) Notice: Subject to any disclaimer, the term of this patent is extended or adjusted under 35 U.S.C. 154(b) by 117 days.

(21) Appl. No.: 16/316,961

(22) PCT Filed: Jul. 18, 2017

(86) PCT No.: PCT/EP2017/068117
§ 371 (c)(1),
(2) Date: Jan. 10, 2019

(87) PCT Pub. No.: WO2018/019656
PCT Pub. Date: Feb. 1, 2018

(65) Prior Publication Data
US 2019/0233907 A1    Aug. 1, 2019

(30) Foreign Application Priority Data
Jul. 19, 2016    (EP) .................................... 16382347

(51) Int. Cl.
| | | |
|---|---|---|
| *C12N 1/20* | (2006.01) | |
| *C12P 7/26* | (2006.01) | |
| *C12P 7/56* | (2006.01) | |
| *C12N 15/03* | (2006.01) | |
| *C12P 7/16* | (2006.01) | |
| *C12P 7/18* | (2006.01) | |
| *C12N 15/01* | (2006.01) | |
| *C12R 1/46* | (2006.01) | |

(52) U.S. Cl.
CPC .............. *C12N 1/205* (2021.05); *C12N 1/20* (2013.01); *C12N 15/01* (2013.01); *C12N 15/03* (2013.01); *C12P 7/16* (2013.01); *C12P 7/18* (2013.01); *C12P 7/26* (2013.01); *C12P 7/56* (2013.01); *C12R 2001/46* (2021.05)

(58) Field of Classification Search
CPC ........ C12R 1/46; C12R 2001/46; C12N 15/03; C12N 15/01; C12N 1/20; C12P 7/18; C12P 7/16; C12P 7/26; C12P 7/56; Y02E 50/10
See application file for complete search history.

(56) References Cited

FOREIGN PATENT DOCUMENTS

| ES | 2352633 A1 | 2/2011 |
| FR | 2777905 A1 | 10/1999 |
| WO | WO 98/07843 A1 | 2/1998 |
| WO | WO 2010/037114 A1 | 4/2010 |
| WO | WO 2013/030280 A1 | 3/2013 |

OTHER PUBLICATIONS

Kaneko et al., Appl Environ Microbiol. 1990, vol. 56, No. 9, p. 2644-2649.*
Crow, V. L., Appl Environ Microbiol. 1990, vol. 56, No. 6, p. 1656-1665.*
Budapest Treaty according to Wikipedia, downloaded on Nov. 17, 2020, 3 pages of PDF.*
International Search Report and Written Opinion dated Jan. 12, 2018 for PCT Application No. PCT/EP2017/068117, 19 pages.
Boumerdassi, et al: "Isolation and Properties of *Lactococcus lactis* subsp. *Lactis* biovar diacetylactis CNRZ 483 Mutants Producing Diacetyl and Acetoin from Glucose", Applied and Environmental Microbiology, Jun. 1997, vol. 63, No. 6, pp. 2293-2299, XP-002086557.

(Continued)

*Primary Examiner* — Kade Ariani
(74) *Attorney, Agent, or Firm* — Squire Patton Boggs (US) LLP

(57) ABSTRACT

The present invention provides a modified strain of the bacterium *Lactococcus lactis* obtainable by a method that comprises a step of fusion of two protoplasts from two *Lactococcus lactis* parental strains which, compared to the wild type strain of *Lactococcus lactis* from which they derive, show: (a) an increased ability to produce acetoin and/or 2,3-butanediol (2,3-BDO), and (b) a decreased ability to produce lactic acid, when cultured under aerobic conditions, and wherein the modified strain of *Lactococcus lactis* has an increased ability to produce 2,3-BDO of at least 20 times the amount produced by the wild type strain, an increased ability to produce acetoin of at least 20 times the amount produced by the wild type strain and a decreased ability to produce lactic acid of at least 10 times the amount produced by the wild type strain, when cultured under aerobic conditions. Also provided are methods to produce acetoin and 2,3-BDO.

8 Claims, No Drawings

(56) References Cited

OTHER PUBLICATIONS

Butanediol (1,4 BDO & 2,3 BDO), 1,3 Butadiene and Methyl Ethyl Ketone (MEK) Market: Applications (THF, PU, PBT, SBR, ABS, NBR Etc.), Bio-Based Alternatives, Downstream Potential, Market Size and Forecast, 2010-2018. Downloaed at https://www.transparencymarketresearch.com/butanediol-butadiene-and-mek-market.html.
Celinska, et al: "Biotechnological production of 2,3-butanediol—Current state and prospects", Biotechnology Advances, Elsevier Publishing, Barking, GB, May 12, 2009, vol. 27, No. 6, pp. 715-725.
Gaspar, et al: "High yields of 2,3-butanediol and mannitol in *Lactococcus lactis* through engineering of NAD+ cofactor recycling", Applied and Environmental Microbiology, Oct. 2011, vol. 77, pp. 6826-6835.
Ge, et al: "Contracted but effective: production of enantiopure 2.3-butanediol by thermophilic and GRAS *Bacillus licheniformis*", Royal Society of Chemistry, Green Chemistry Paper, May 27, 2016, 11 pages.
Gokhale, et al: "Protoplast Fusion: A Tool for Intergeneric Gene Transfer in Bacteria", Biotechnology Advances 1993, vol. 11, No. 2, pp. 199-217, XP-023929954.
Hässler, et al: "Enhanced fed-batch fermentation of 2, 3-butanediol by *Paenibacillus polymyxa* DSM 365", Bioresource Technology, Aug. 19, 2012, vol. 124, pp. 237-244.
Lian, et al: "Metabolic engineering of a *Saccharomyces cerevisiae* strain capable of simultaneously utilizing glucose and galactose to produce enantiopure (2R, 3R)-butanediol", Metabolic Engineering, Feb. 10, 2014, vol. 23, pp. 92-99.
Liu, et al: "Combining metabolic engineering and biocompatible chemistry for high-yield production of homo-diacetyl and homo-(S,S)-2,3-butanediol", Metabolic Engineering 2016, vol. 36, pp. 57-67.
Nielsen, et al. "Metabolic Engineering of Acetoin and meso-2,3-Butanediol Biosynthesis in *E. coli*", Biotechnology Journal 2010, vol. 5, pp. 274-284.
Peberdy, et al: "Protoplast fusion—a tool for genetic manipulation and breeding in industrial microorganisms", Enzyme Microbial Technology, Jan. 1980, vol. 2., No. 1, pp. 23-29, XP-023677937.
Platteeuw, et al: "Metabolic engineering of *Lactococcus lactis*: influence of the over production of alpha-acetolactate synthase in strains deficient in lactate dehydrogenase as a function of culture conditions", Applied and Environmental Microbiology, Nov. 1995, vol. 61, No. 11, pp. 3967-3971.
Roncal, et al: Poster "Acetoin overproduction by a mutant strain of *Lactococcus lactis*", ANQUE•ICCE•Biotec 2014 Conference, May 2014. https://www.researchgate.net/publication/303471166, 2 pages.
Roncal, et al: "Efficient production of acetoin by fermentation using new isolated mutant strain *Lactococcus lactis* subsp. *lactis* CML B4", Process Biochemistry, Apr. 6, 2017, vol. 58, pp. 35-41.
Terzaghi, et al: "Improved medium for Lactic Streptococci and their bacteriophages", Applied Microbiology, Jun. 1975, vol. 29, No. 6, pp. 807-813.
Zhang, et al. "Genome shuffling leads to rapid phenotypic improvement in bacteria", Nature, Feb. 7, 2002, vol. 415, pp. 644-646.

* cited by examiner

BACTERIAL STRAIN PRODUCING 2,3-BUTANEDIOL AND OTHER METABOLITES

This application claims the benefit of European Patent Application EP16382347.9 filed Jul. 19, 2016.

FIELD OF THE INVENTION

The present invention belongs to the field of microorganisms obtained by genetic manipulation. In particular, this invention is related to a new lactic acid bacterial strain belonging to the species *Lactococcus lactis*, characterized by a high capacity to produce 2,3-butanediol and acetoin, molecules that have wide-ranging applications in the chemical, pharmaceutical and biofuel industries.

BACKGROUND ART 2,3-Butanediol (2,3-BDO) is a chemical that shows a great potential in the fields of fuels and chemicals, including uses as a building block in the manufacture of a wide range of chemicals. It can be used as solvent, antifreeze agent, liquid fuel and monomer for the manufacture of many synthetic polymers and resins. It has a heating value of 27,200 J $g^{-1}$, similar to that of ethanol (29,100 J $g^{-1}$) and methanol (22,100 J $g^{-1}$), which make it suitable as liquid fuel and fuel additive. Moreover, due to its high octane number, it could serve as an octane booster for petrol. 2,3-BDO also finds additional potential applications in the production of printing inks, perfumes, fumigants, spandex, moistening and softening agents, plasticizers and as a carrier for pharmaceuticals.

Of special relevance are the uses of 2,3-BDO as building block, that is, as precursor in the synthesis of valuable industrial chemicals, including acetoin and diacetyl, methyl ethyl ketone, 2-butanol, butenes, 1,3-butadiene and plastics (polyesters, polycarbonates and polyurethanes). Among them, 1,3-butadiene deserves special attention because it is the monomer for the synthesis of synthetic rubber, mainly used in the manufacture of tires. In addition, some of the above derivatives can be converted, by means of oligomerization, condensation and hydrogenation reactions, into higher hydrocarbons with potential uses as (bio)fuels, including jet fuels.

Commercially, the key downstream products of 2,3-BDO have a potential global market of around 32 million tons per annum, valued at approximately $43 billion in sales.

Currently, industrial production of 2,3-BDO is mainly made from petrochemical feedstocks, by means of a complex and costly process. During oil refining, after removal of butadiene and isobutene from crack gases, a C4 hydrocarbon fraction, called C4 raffinate II, is obtained, which contains approximately 77% butenes and 23% of a mixture of butane and isobutane. By chlorohydrination of this fraction with a solution of chlorine in water and subsequent cyclization of the chlorohydrins with sodium hydroxide, a butene oxide mixture of the following composition is obtained: 55% trans-2,3-butene oxide, 30% cis-2,3-butene oxide, and 15% 1,2-butene oxide. Hydrolysis of this mixture at 160-220° C. under 50 bar pressure yields a mixture of butanediols which is separated by vacuum fractionation. By this reaction sequence, meso-2,3-butanediol is obtained from trans-2-butene via trans-2,3-butene oxide; the racemic mixture of R,R- and S,S-2,3-butanediol is formed analogously from cis-2-butene via cis-2,3-butene oxide.

2,3-BDO is currently an unattractive market segment due to its costly chemical synthesis. The raw material price and the environmental impact of using synthetic 2,3-BDO is acting as major barriers to the growth of the global 2,3-BDO market. Owing to these concerns, tendencies are shifting towards the search for more environmentally friendly and cost competitive alternatives and, among them, biological production of 2,3-BDO appears in an outstanding place (http://www.transparencymarketresearch.com; Butanediol (1,4 BDO & 2,3 BDO), 1,3 Butadiene and MEK Market: Applications (THF, PU, PBT, SBR, ABS, NBR etc.), Bio-based Alternatives, Downstream Potential, Market Size and Forecast, 2010-2018).

Many microorganisms are known to produce 2,3-BDO, but only a few of them make it in quantities high enough to be potentially considered as industrially relevant. The best producers are bacteria belonging to the genera *Klebsiella*, *Enterobacter*, *Bacillus* and *Serratia*, especially *Klebsiella pneumoniae* and *Klebsiella oxytoca*.

The metabolic pathway involved in the biosynthesis of 2,3-BDO starts with pyruvate resulting from sugar metabolism and comprises three steps. In the first step, the thiamine-dependent enzyme α-acetolactate synthase catalyzes the condensation of two molecules of pyruvate yielding a molecule of α-acetolactate and releasing a molecule of $CO_2$. α-Acetolactate is then converted into acetoin by a decarboxylation reaction catalyzed by α-acetolactate decarboxylase. Finally, acetoin is reduced to 2,3-BDO by acetoin reductase/2,3-BDO dehydrogenase using NADH as cofactor.

Regarding an industrial-scale production of 2,3-BDO by fermentation, the fact that the best producers, *K. pneumoniae* and *K. oxytoca*, are pathogenic bacteria (Risk Group 2—RG2) is a cause of strong concern. Industrial-scale fermentation processes require following strict safety measures, implying that the use of RG2 microorganisms is an obstacle for industrial development of said fermentation processes. When fermenting volumes larger than 10 L using RG2 microorganisms, appropriate biosafety measures must be adopted, including Biosafety Level 2 Large Scale (BSL2-LS) containment facility design and special operational procedures. All these biosafety measures significantly increase production costs, which have been estimated to be increased by 10-30%, only considering fermenter basic cost, per each increment in the containment level.

Therefore, there is a need for RG1 microorganisms (safe) able to produce 2,3-BDO as efficiently as the aforementioned RG2 bacteria. Several RG1 bacteria have been reported to produce 2,3-BDO, but, in general, their efficiency was too low for an economic process. Some important exceptions would be the bacteria *Paenibacillus polymyxa* (Hässler, T., et al. "Enhanced fed-batch fermentation of 2, 3-butanediol by *Paenibacillus polymyxa* DSM 365" Bioresource technology 2012 vol. 124, pp. 237-244) and *Bacillus licheniformis* (Ge, Y., et al. "Contracted but effective: production of enantiopure 2,3-butanediol by thermophilic and GRAS *Bacillus licheniformis*". Green Chemistry, 2016).

As an alternative, production of 2,3-BDO has been engineered in the bacterium *Escherichia coli* (Nielsen, D. R., et al. "Metabolic Engineering of Acetoin and meso-2,3-Butanediol Biosynthesis in *E. coli*.", Biotechnol. J. 2010, vol. 5, pp. 274-284) and the yeast *Saccharomyces cerevisiae* (Lian, J., et al. "Metabolic engineering of a *Saccharomyces cerevisiae* strain capable of simultaneously utilizing glucose and galactose to produce enantiopure (2R, 3R)-butanediol" Metabolic engineering 2014, vol. 23, pp. 92-99). Another possibility to be considered is the use of RG1 natural producers, improving their 2,3-BDO synthesis capacities. Within this last alternative the lactic acid bacterium *Lactococcus lactis* appears as a possible candidate.

*L. lactis* shows several advantageous features to be used in industrial processes: it has a small sized, well characterized, genome, which has been sequenced for several strains; a wide range of tools are available for its genetic manipulation; it shows a fast growth under either aerobic or anaerobic conditions; it displays a high glycolytic flux; it has a rather simple energy and carbon metabolism; it has different metabolic pathways for the production of interesting chemicals; it is not a pathogen and it is considered a GRAS (Generally Recognized As Safe) organism, which allows it to be used in food applications. Leaving aside food uses, that have their own characteristics, all these features make *L. lactis* a highly suitable host for development of cell factories intended for the efficient industrial production of valuable chemicals by fermentation.

*L. lactis* is a facultative anaerobe characterized by producing lactic acid as the main product of carbohydrate fermentation (homolactic fermentation). Under certain conditions, nevertheless, this bacterium can also carry out a heterolactic or mixed-acid fermentation, producing a different profile of metabolites, including 2,3-BDO. However, although *L. lactis* contains a complete metabolic pathway for 2,3-BDO biosynthesis, natural production of this metabolite is generally residual.

There are a few reports describing the use of metabolic engineering to increase the production of 2,3-BDO in *L. lactis* (Platteeuw C, et al. "Metabolic engineering of *Lactococcus lactis*—influence of the overproduction of alpha-acetolactate synthase in strains deficient in lactate-dehydrogenase as a function of culture conditions", Appl. Environ. Microbiol. 1995, vol. 61, pp. 3967-71; Gaspar P, et al. "High yields of 2,3-butanediol and mannitol in *Lactococcus lactis* through engineering of NAD(+) cofactor recycling", Appl. Environ. Microbiol. 2011, vol. 77, pp. 6826-35; Liu J, et al. "Combining metabolic engineering and biocompatible chemistry for high-yield production of homo-diacetyl and homo-(S,S)-2,3-butanediol", Metabolic engineering 2016, vol. 36, pp. 57-67) and other lactic acid bacteria (Enhanced pyruvate to 2,3-butanediol conversion in lactic acid bacteria, PCT/US2009/058834). All of them lie, on the one hand, in the inactivation of competitive pathways, specially L-lactate dehydrogenase and, on the other hand, in the overexpression of the genes of the 2,3-BDO pathway.

Production of 2,3-BDO by these recombinant strains requires that they are cultured in media containing antibiotics to maintain the foreign genetic material introduced into them, and/or compounds such as nisin, that induce an increased gene expression, or hemin and $Fe^{3+}$, to sustain growth. In any case, culture media must be supplemented with expensive ingredients that increase operational costs to a level hardly compatible with an economically efficient industrial process.

The state of the art lacks, therefore, efficient methods of sustainable biotechnological 2,3-BDO production, by means of RG1 microorganism-driven fermentations, that allow to obtain high concentrations of 2,3-BDO with large yields and productivities, from renewable biomass raw materials.

DETAILED DESCRIPTION OF THE INVENTION

With the aim of solving this deficiency, the present invention provides a RG1 bacterial strain with an enhanced capacity to produce 2,3-BDO, a method to obtain said strain, and an efficient fermentation method using said strain, with high yields and productivities, and industrially feasible. In addition, surprisingly, this same strain has been found to produce other alternative metabolites, specially acetoin and lactic acid, depending on the culture conditions used.

The present invention provides a *L. lactis* strain, belonging to RG1, that shows a high ability to produce metabolites such as 2,3-BDO, acetoin and lactic acid, depending on culture conditions. The strain displays a surprising versatility regarding metabolite production, without affecting its viability and functionality.

As illustrated below, the strain of the present invention is highly efficient and specific in relation to the production of the aforementioned metabolites, depending on the medium conditions. For example, using the strain to ferment a carbohydrate-rich culture medium, and simply adjusting pH and oxygen concentration parameters, the strain of the present invention is able to produce mainly either 2,3-BDO, acetoin or lactic acid. It is important to point out that these features are achieved without the need of supplementing culture medium with compounds such as antibiotics, nisin and other that promote the synthesis of the said products. This point is very important, because it allows to cheapen production costs and to simplify the handling and fermentation steps of the process. In conclusion, it makes easier metabolite production at an industrial scale.

In order to obtain the strain of this invention, inventors have exploited a procedure that comprises protoplast fusion of two genetically modified *L. lactis* strains. This procedure is known as genome shuffling and allows genetic recombination of two mutants (Zhang Y X, et al. "Genome shuffling leads to rapid phenotypic improvement in bacteria", Nature 2002, vol. 415, pp. 644-646). Surprisingly, by means of this protoplast fusion, a new strain of *L. lactis*, having a high ability to produce metabolites, has been found. Advantageously, using the technology of protoplast fusion, neither the insertion into the bacteria of exogenous DNA sequences nor the use of chemical inducers of gene expression are required.

Thus, a first aspect of the invention is a method to produce a modified strain of the bacterium *Lactococcus lactis* that comprises a step of fusion of two protoplasts from two *Lactococcus lactis* parental strains which, compared to a wild type strain of *Lactococcus lactis*, show: (a) an increased ability to produce acetoin and/or 2,3-butanediol, and (b) a decreased ability to produce lactic acid, when cultured under aerobic conditions.

As disclosed by the experimental data provided, the strain resulting from this procedure can show, depending on culture conditions, an increased ability to produce 2,3-BDO and, on the contrary, a decreased ability to produce lactic acid, when compared to its parental strains.

In a particular embodiment of the first aspect of the invention, each of the aforesaid *L. lactis* parental strains, having an increased ability to produce acetoin and/or 2,3-BDO and a decreased ability to produce lactic acid when cultured under aerobic conditions, is obtained by subjecting a wild type strain of *L. lactis* to mutagenesis.

In another particular embodiment of the first aspect of the invention, mutagenesis treatment is carried out by random mutagenesis.

In another particular embodiment of the first aspect of the invention, mutagenesis treatment is carried out using chemical mutagens.

In another particular embodiment of the first aspect of the invention, mutagenesis treatment is carried out using ethyl methanesulfonate (EMS).

In another particular embodiment of the first aspect of the invention, mutagenesis treatment is carried out using radiation.

In another particular embodiment of the first aspect of the invention, mutagenesis treatment is carried out using recombinant DNA technologies or genetic engineering.

In another particular embodiment of the first aspect of the invention, the strains resulting from mutagenesis treatment are selected in an acidic agar nutritive medium with reduced buffering capacity and supplemented with 2,3,5-triphenyl tetrazolium (as described in the patents FR2777905 and ES2352633B1). High lactate producing bacteria growing in this selection medium form pink colonies and it is expected that low lactate producers appear as red/brown colonies.

In another particular embodiment of the first aspect of the invention, one of the parental strains has an increased ability to produce acetoin and the other one has an increased ability to produce 2,3-BDO, both compared to a wild type strain, when cultured under aerobic conditions.

In another particular embodiment of the first aspect of the invention, the starting wild type strain, which is subjected to the mutagenesis treatment, is the strain *Lactococcus lactis* NCIMB 702118, deposited in the National Collection of Industrial, Marine and Food Bacteria (UK).

In another particular embodiment of the first aspect of the invention, one of the two parental strains used in the protoplast fusion step is the strain *Lactococcus lactis* CML B4, which has an increased ability to produce acetoin and a decreased ability to produce lactic acid, compared to a wild type strain of *Lactococcus lactis*, when cultured under aerobic conditions. The strain *Lactococcus lactis* CML B4 was deposited by the applicant, according to the Budapest Treaty, on Apr. 21, 2009 in the Colección Española de Cultivos Tipo (CECT), located at Universidad de Valencia, Edificio de Investigación, Campus de Burjassot, 46100 Burjasot (Valencia) Spain. This strain of *L. lactis* was identified by the depositor with the reference *Lactococcus lactis* subsp. *lactis* CML B4, and received the accession number CECT 7512, and was, in addition, declared as viable.

In another particular embodiment of the first aspect of the invention, one of the two parental strains used in the protoplast fusion step is the strain *Lactococcus lactis* CML B3, which has an increased ability to produce 2,3-BDO and acetoin and a decreased ability to produce lactic acid, compared to a wild type strain of *Lactococcus lactis*, when cultured under aerobic conditions.

In another particular embodiment of the first aspect of the invention, the parental strain having an increased ability to produce acetoin and a decreased ability to produce lactic acid, compared to a wild type strain of *Lactococcus lactis* when cultured under aerobic conditions, used in the protoplast fusion step, is the strain *Lactococcus lactis* CML B4, deposited at the Spanish Type Culture Collection under accession number CECT 7512, and the parental strain having an increased ability to produce 2,3-BDO and a decreased ability to produce lactic acid, compared to a wild type strain of *Lactococcus lactis* when cultured under aerobic conditions, used in the protoplast fusion step, is the strain *Lactococcus lactis* CML B3.

In another particular embodiment of the first aspect of the invention, the parental strain having an increased ability to produce acetoin and a decreased ability to produce lactic acid, compared to a wild type strain of *Lactococcus lactis* when cultured under aerobic conditions, used in the protoplast fusion step, is the strain *Lactococcus lactis* CML B4, deposited at the Spanish Type Culture Collection under accession number CECT 7512, and the parental strain having an increased ability to produce 2,3-BDO and a decreased ability to produce lactic acid, compared to a wild type strain of *Lactococcus lactis* when cultured under aerobic conditions, used in the protoplast fusion step, is the strain *Lactococcus lactis* CML B3, being both CML B4 and CML B3 strains derived from the wild type strain NCIMB 702118.

In another particular embodiment of the first aspect of the invention, the procedure comprises the following steps: 1) a wild type strain of *L. lactis* is subjected to a mutagenesis treatment; 2) two strains obtained in the step 1) are selected, which have, when cultured under aerobic conditions, an increased ability to produce acetoin and/or 2,3-BDO and a decreased ability to produce lactic acid, compared to the wild type strain; 3) the two strains selected in the step 2) are used as parental strains in a protoplast fusion step.

In another particular embodiment of the first aspect of the invention, the procedure comprises the following steps: 1) the wild type strain *L. lactis* NCIMB 702118 is subjected to a mutagenesis treatment; 2) two strains obtained in the step 1) are selected, which have, when cultured under aerobic conditions, an increased ability to produce acetoin and/or 2,3-BDO and a decreased ability to produce lactic acid, compared to the wild type strain; 3) the two strains selected in the step 2) are used as parental strains in a protoplast fusion step.

In another particular embodiment of the first aspect of the invention, the procedure comprises the following steps: 1) the wild type strain *L. lactis* NCIMB 702118 is subjected to a chemical mutagenesis treatment by exposing to EMS; 2) two strains obtained in the step 1) are selected, which have, when cultured under aerobic conditions, an increased ability to produce acetoin and/or 2,3-BDO and a decreased ability to produce lactic acid, compared to the wild type strain; 3) the two strains selected in the step 2) are used as parental strains in a protoplast fusion step.

In another particular embodiment of the first aspect of the invention, the procedure comprises the following steps: 1) the wild type strain *L. lactis* NCIMB 702118 is subjected to a chemical mutagenesis treatment by exposing to EMS; 2) two strains obtained in the step 1) are selected, one of them having an increased ability to produce acetoin and a decreased ability to produce lactic acid and the other one having an increased ability to produce 2,3-BDO and a decreased ability to produce lactic acid, both compared to the wild type strain, when cultured under aerobic conditions; 3) the two strains selected in the step 2) are used as parental strains in a protoplast fusion step.

A second aspect of the invention is a modified strain of the bacterium *L. lactis* obtainable by the method described in the first aspect of the invention.

In a particular embodiment of the second aspect of the invention, the strain has an increased ability to produce 2,3-BDO of at least 10 times the amount produced by the wild type strain, when cultured under aerobic conditions.

In another particular embodiment of the second aspect of the invention, the strain has an increased ability to produce 2,3-BDO of at least 20 times the amount produced by the wild type strain, when cultured under aerobic conditions.

In another particular embodiment of the second aspect of the invention, the strain has an increased ability to produce acetoin of at least 10 times the amount produced by the wild type strain, when cultured under aerobic conditions.

In another particular embodiment of the second aspect of the invention, the strain has an increased ability to produce acetoin of at least 20 times the amount produced by the wild type strain, when cultured under aerobic conditions.

In another particular embodiment of the second aspect of the invention, the strain has a decreased ability to produce lactic acid of at least 10 times the amount produced by the wild type strain, when cultured under aerobic conditions.

In another particular embodiment of the second aspect of the invention, the strain has a decreased ability to produce lactic acid of at least 20 times the amount produced by the wild type strain, when cultured under aerobic conditions.

In another particular embodiment of the second aspect of the invention, the strain has an increased ability to produce 2,3-BDO of at least 10 times the amount produced by the wild type strain, and a decreased ability to produce lactic acid of at least 10 times the amount produced by the wild type strain, when cultured under aerobic conditions.

In another particular embodiment of the second aspect of the invention, the strain has an increased ability to produce 2,3-BDO of at least 20 times the amount produced by the wild type strain, and a decreased ability to produce lactic acid of at least 20 times the amount produced by the wild type strain, when cultured under aerobic conditions.

In another particular embodiment of the second aspect of the invention, the strain of the bacterium *L. lactis* is identified as *Lactococcus lactis* 43103, which is deposited at the Spanish Type Culture Collection (CECT) under accession number CECT 9139. The strain of *L. lactis* of the invention was deposited, according to the requirements of the Budapest Treaty, on Apr. 19, 2016 in the Spanish Type Culture Collection (CECT), located in the Universidad de Valencia C.P 46980 Catedrático Agustín Escardino, num. 9, Paterna, Valencia (Spain), by the depositor Fundación Tecnalia Research & Innovation, located in the Parque Tecnológico de San Sebastian, Mikeletegi Pasealekua, num. 2, E-20009 Donostia-San Sebastián (Spain).

The strain of *L. lactis* was identified by the depositor with the reference 43103, and received the accession number CECT 9139, and was, in addition, declared as viable. Its name is specifically *L. lactis* 43103.

A third aspect of the invention is a method of production of 2,3-BDO that comprises the aerobic fermentation of a carbohydrate-rich culture medium by the bacterial strain of the second aspect of the invention.

In a particular embodiment of the third aspect of the invention, the method of 2,3-BDO production comprises the following steps:
(a) Pre-culture of a strain as defined in the second aspect of the invention;
(b) Inoculation of a carbohydrate-rich culture medium with the pre-culture obtained in step (a);
(c) Fermentation of carbohydrates present in the culture medium inoculated in step (b) at 20-40° C.; pH 5.0-7.5 and 5-100% dissolved oxygen concentration; and
(d) Separation of cells from the fermented broth resulting from step (c).

It should be noted that dissolved oxygen concentration is expressed as the % with respect to medium saturation concentration.

In another particular embodiment of the third aspect of the invention, the method of 2,3-BDO production comprises the following steps:
(a) Pre-culture of a strain as defined in the second aspect of the invention;
(b) Inoculation of a carbohydrate-rich culture medium with the pre-culture obtained in step (a);
(c) Fermentation of carbohydrates present in the culture medium inoculated in step (b) at 20-40° C.; pH 5.0-7.5 and 10-90% dissolved oxygen concentration; and
(d) Separation of cells from the fermented broth resulting from step (c).

In another particular embodiment of the third aspect of the invention, the method of 2,3-BDO production comprises the following steps:
(a) Pre-culture of a strain as defined in the second aspect of the invention;
(b) Inoculation of a carbohydrate-rich culture medium with the pre-culture obtained in step (a);
(c) Fermentation of carbohydrates present in the culture medium inoculated in step (b) at 20-40° C.; pH 5.5-6.0 and 5-100% dissolved oxygen concentration; and
(d) Separation of cells from the fermented broth resulting from step (c).

In another particular embodiment of the third aspect of the invention, the method of 2,3-BDO production comprises the following steps:
(a) Pre-culture of a strain as defined in the second aspect of the invention;
(b) Inoculation of a carbohydrate-rich culture medium with the pre-culture obtained in step (a);
(c) Fermentation of carbohydrates present in the culture medium inoculated in step (b) at 20-40° C.; pH 5.5-6.0 and 10-90% dissolved oxygen concentration; and
(d) Separation of cells from the fermented broth resulting from step (c).

In another particular embodiment of the third aspect of the invention, the method of 2,3-BDO production comprises, additionally, a step of purification of the 2,3-BDO present in the cell-free fermentation broth resulting from step (d).

In another particular embodiment of the third aspect of the invention, fermentation carried out in step (c) is in continuous mode.

In another particular embodiment of the third aspect of the invention, fermentation carried out in step (c) is in fed-batch mode.

In another particular embodiment of the third aspect of the invention, fermentation carried out in step (c) is in batch mode.

2,3-BDO is accumulated in the fermentation broth for 15-48 hours, preferably for 20-40 hours from the start of the culture that occurs at the moment of inoculation. When maximal 2,3-BDO production is attained, that occurs shortly after microorganism has consumed all the carbohydrate available as carbon source, fermentation can be considered completed. Once fermentation is finished, cells of the strain of the second aspect of the invention can be separated from fermentation broth. This process can be done preferably by means of physical methods, such as centrifugation, filtration or any other available in the art.

Fermentation-produced 2,3-BDO, that is dissolved in the clarified fermentation broth, can be then recovered or purified or used as it is as an aqueous solution, in the latter case either without further modification or after a process of concentration. Purification, when carried out, can be done using any method known in the art, either alone or combining some of them, including but not limited to distillation, pervaporation, ultrafiltration, nanofiltration, direct osmosis, liquid-liquid extraction, solid phase extraction, supercritical fluid extraction, chromatography, and others.

A fourth aspect of the invention is a method of acetoin production that comprises the aerobic fermentation of a carbohydrate-rich culture medium by the bacterial strain of the second aspect of the invention.

Surprisingly, it has been found that the metabolite production profile of the strain of the second aspect of the invention depends very much on culture conditions. It mainly produces 2,3-BDO when fermentation is carried out under aerobic conditions at a slightly acidic pH value, between 5.5 and 6.0.

However, when fermentation is carried out also under aerobic conditions, but at a higher pH value, close to neutrality, the main fermentation product is acetoin. By "mainly" it is understood that the referred metabolite accounts for 45-95%, preferably 65-95%, of the totality of fermentation products. In particular, 70-95%, preferably, 80-95%, of the fermentation products correspond to 2,3-BDO when fermentation is carried out at pH 5.5-6.0. When fermentation is carried out at pH 6.5-7.0, the strain produces acetoin in an amount corresponding from 45 to 95%, preferably, from 65 to 80%, of the fermentation products.

In a particular embodiment of the fourth aspect of the invention, the method of acetoin production comprises the following steps:
(a) Pre-culture of a strain as defined in the second aspect of the invention;
(b) Inoculation of a carbohydrate-rich culture medium with the pre-culture obtained in step (a);
(c) Fermentation of carbohydrates present in the culture medium inoculated in step (b) at 20-40° C.; pH 6.5-7.5 and 30-100% dissolved oxygen concentration; and
(d) Separation of cells from the fermented broth resulting from step (c).

In another particular embodiment of the fourth aspect of the invention, the method of acetoin production comprises, additionally, a step of purification of the acetoin present in the cell-free fermentation broth resulting from step (d).

In another particular embodiment of the fourth aspect of the invention, fermentation carried out in step (c) is in continuous mode.

In another particular embodiment of the fourth aspect of the invention, fermentation carried out in step (c) is in fed-batch mode.

In another particular embodiment of the fourth aspect of the invention, fermentation carried out in step (c) is in batch mode.

Acetoin is accumulated in the fermentation broth for 15-40 hours, preferably for 18-24 hours from the start of the culture that occurs at the moment of inoculation. When maximal acetoin production is attained, that occurs shortly after microorganism has consumed all the carbohydrate available as carbon source, fermentation can be considered completed.

A fifth aspect of the invention is a method of lactic acid production that comprises the anaerobic fermentation of a carbohydrate-rich culture medium by the bacterial strain of the second aspect of the invention.

In a particular embodiment of the fifth aspect of the invention, the method of lactic acid production comprises the following steps:
(a) Pre-culture of a strain as defined in the second aspect of the invention;
(b) Inoculation of a carbohydrate-rich culture medium with the pre-culture obtained in step (a);
(c) Fermentation of carbohydrates present in the culture medium inoculated in step (b) at 20-40° C.; pH 6.0-7.5 and under anaerobic conditions; and
(d) Separation of cells from the fermented broth resulting from step (c).

In another particular embodiment of the fifth aspect of the invention, the method of lactic acid production comprises, additionally, a step of purification of the lactic acid present in the cell-free fermentation broth resulting from step (d).

In another particular embodiment of the fifth aspect of the invention, fermentation carried out in step (c) is in continuous mode.

In another particular embodiment of the fifth aspect of the invention, fermentation carried out in step (c) is in fed-batch mode.

In another particular embodiment of the fifth aspect of the invention, fermentation carried out in step (c) is in batch mode.

Lactic acid is accumulated in the fermentation broth for 15-40 hours, preferably for 20-30 hours from the start of the culture that occurs at the moment of inoculation. When maximal lactic acid production is attained, that occurs shortly after microorganism has consumed all the carbohydrate available as carbon source, fermentation can be considered completed.

In a particular embodiment of the third, fourth and fifth aspects of the invention, the fermentable carbohydrate is selected, without limiting purposes, from the group of glucose, xylose, fructose, mannose, galactose, sucrose, lactose, molasses, and mixtures thereof.

In another particular embodiment of the third, fourth and fifth aspects of the invention, the fermentation medium contains a nitrogen source selected, without limiting purposes, from the group of yeast extract, meat extract, corn steep liquor (CSL), meat, soybean or casein peptones, protein hydrolysates from protein-rich agro-food by-products, such as soybean meal/flour, whey, dry distillers grains with solubles (DDGS), and mixtures thereof.

In another particular embodiment of the third, fourth and fifth aspects of the invention, the culture medium can be supplemented with additional nutrients and growth factors, such as vitamins and mineral salts, in order to assist bacterial growth and promote 2,3-BDO production. Vitamins to be used include, among others, pyridoxamine, biotin, nicotinic acid, calcium pantothenate, riboflavin and lipoic acid, that can be added either as artificial mixtures of pure vitamins with known composition or as complex natural preparations or extracts containing them, such as yeast extract, CSL or others. Mineral salts can be preferably selected from the group of phosphates, and potassium and magnesium salts.

In another particular embodiment of the third, fourth and fifth aspects of the invention, the carbohydrate-rich medium can also be supplemented, if necessary because of an excessive foam formation throughout the fermentation, with an antifoam agent, such as silicone-based ones, vegetable oils, polyethylene glycol and the like, according to known procedures in the art.

In another particular embodiment of the third and fourth aspects of the invention, culture of the strain of the second aspect of the invention in the carbohydrate-rich medium can be carried out using any standard technology of aerobic culture. Culture methods in liquid media are preferred, specially shaken flask cultures or cultures in fermenter- or chemostat-like reactors.

In another particular embodiment of the third and fourth aspects of the invention, the aerobic characteristics of the culture can be achieved by means of an adequate supply of oxygen to the culture medium, either in the form of air, pure oxygen or mixtures of them. In the case of shaken flask cultures, oxygen supply is achieved through the shaking of culture flasks at frequencies between 100 and 500 rpm, preferably between 200 and 300 rpm. In the case of culture reactors, oxygen supply can be achieved by passing through the culture medium a flow of either air, pure oxygen or mixtures of them, in such a way that dissolved oxygen concentration is between 5 and 100%, preferably between 10 and 90%, of saturation concentration. Culture medium mixing can be carried out with the aid of either a stirrer or impeller, operating at 250-1000 rpm, preferably at 500-750 rpm.

In a particular embodiment of the fifth aspect of the invention, culture of the strain of the second aspect of the invention in the carbohydrate-rich medium can be carried out using any standard technology of anaerobic culture. Culture methods in liquid media are preferred, especially flask cultures or cultures in fermenter- or chemostat-like reactors.

In another particular embodiment of the fifth aspect of the invention, the anaerobic characteristics of the culture can be achieved by isolating the culture medium from ambient oxygen. In the case of flask cultures, isolation can be achieved by either the lack of shaking or hermetically sealing them.

In the case of culture reactors, isolation can be achieved by either hermetically sealing them and/or passing through the culture medium a flow of oxygen-free gases. Medium mixing in culture reactors can be carried out with the aid of either a stirrer or impeller, operating at 250-1000 rpm, preferably at 400-600 rpm.

In another particular embodiment of the third, fourth and fifth aspects of the invention, medium pH control, when necessary to maintain pH at a fixed value, can be achieved by either the use of a buffering agent, selected among those usually used for that purpose, or the addition of either an alkali or acid, depending on the particular needs of the culture, in order to counteract acidification or alkalinization, respectively, that could cause microbial growth.

The invention thus also provides a modified strain of *Lactococcus lactis* that has an increased ability to produce 2,3-BDO of at least 10 times, preferably, 20 times the amount produced by the wild type strain from which it derives, an increased ability to produce acetoin of at least 10 times, preferably, 20 times the amount produced by the wild type strain from which it derives and a decreased ability to produce lactic acid of at least 10 times the amount produced by the wild type strain from which it derives, when cultured under aerobic conditions. Alternatively or additionally, the strain of the invention produces mainly 2,3-BDO or acetoin depending on the pH of the culture. For example, the strain of the invention produces 2,3-BDO in an amount corresponding from 70 to 95% of the total fermentation products when cultured on a carbohydrate-rich medium at 20-40° C., pH 5.5-6.0 and 5-100% dissolved oxygen concentration and produces acetoin in an amount corresponding from 45 to 80% of the fermentation products when cultured on a carbohydrate-rich medium at 20-40° C., pH 6.5-7.5 and 30-100% dissolved oxygen concentration. Preferably, the strain of the invention produces 2,3-BDO in an amount corresponding from 80 to 95% of the total fermentation products when cultured on a carbohydrate-rich medium at 20-40° C., pH 5.5-6.0 and 10-90% dissolved oxygen concentration and produces acetoin in an amount corresponding from 65 to 80% of the fermentation products when cultured on a carbohydrate-rich medium at 20-40° C., pH 6.8-7.2 (for example pH 7) and 30-100% dissolved oxygen concentration. The wild type strain of *Lactococcus lactis* may be *Lactococcus lactis* NCIMB 702118. Further, the strain of the invention is obtainable by protoplast fusion of two 2,3-BDO and/or acetoin overproducing *L. lactis* parental strains which are derived from a wild type strain as disclosed above. The wild type strain may be *Lactococcus lactis* NCIMB 702118.

With the aim of increasing the clarity of the subject described herewith, the following definitions are provided, that should be applied throughout the whole document and especially in the claims.

The term "genome shuffling", as used herein, refers to a method based on the mixing of genomes of two or more strains or microorganisms into one, following a protoplast fusion and recombination process. Recombination ultimately occurs randomly, which enables to generate a large library of recombinant derivative strains showing a wide range of genomes and phenotypes. Recombinant strains can be further subjected to a selection or screening process in order to only isolate those strains endowed with the sought phenotypic characteristics and properties. Typically, "genome shuffling" is carried out using two or more mutant strains showing some genetic diversity in order to search for advantageous combinations of these diversities.

The term "wild type strain", as used herein, refers to a microbial strain as found in nature, that is, a strain that has not been manipulated by man through any technology in order to modify its genetic and phenotypic features.

The term "pre-culture", as used herein, refers to a preliminary small-scale culture of the strain used to inoculate the broth wherein fermentation will be carried out. The pre-culture of the strain of the second aspect of the invention can be carried out for 24 hours in YEC medium, under the aerobic culture conditions explained below in the section of General Methods.

The term "carbohydrate-rich culture medium", as used herein, refers to any culture medium containing energy, carbon and nitrogen sources assimilable by the strain of the second aspect of the invention, and that allows its growth and a high production of either 2,3-BDO, acetoin or lactic acid, depending on culture conditions, by the same. For example and without limiting purposes, among suitable carbon and energy sources are found glucose, xylose, fructose, mannose, galactose, sucrose, lactose, molasses, and mixtures thereof. As suitable nitrogen sources can be included, without being limited to them, yeast extract, meat extract, corn steep liquor (CSL), meat, soybean or casein peptones, protein hydrolysates from protein-rich agro-food by-products, such as soybean meal/flour, whey, dry distillers grains with solubles (DDGS), and mixtures thereof.

The term "protoplast", as used herein, refers to a bacterial cell deprived of its cell wall by enzyme treatment in an osmotically stabilized medium.

The term "aerobic fermentation", as used herein, refers to a fermentation carried out under aerobic conditions, that is, in the presence of oxygen. The term "anaerobic fermentation", as used herein, refers to a fermentation carried out under anaerobic conditions, that is, in the absence of oxygen. Fermentation, in a broad sense, is a metabolic process that converts carbohydrates into various bio-products.

The term "increased ability to produce acetoin and/or 2,3-BDO compared to the wild type strain of *L. lactis*", as used herein about a modified strain, refers to the fact that the aforesaid strain produces a larger amount of such metabolites (acetoin and/or 2,3-BDO) than the wild type strain as is detected in the examples provided in this invention by using the methods described in the General methods section.

The term "decreased ability to produce lactic acid compared to the wild type strain of *L. lactis*", as used herein about a modified strain, refers to the fact that the aforesaid strain produces a lower amount of such metabolite (lactic acid) than the wild type strain as is detected in the examples provided in this invention by using the methods described in the General methods section.

EXAMPLES

The present invention is further illustrated by means of the following examples, which are only given with illustrative purposes and are not intended to limit the invention in any way.

General Methods

Microorganisms:

Microorganisms used in this invention were the bacterial strains *L. lactis* CML B4 (Spanish patent ES2352633B1), *L. lactis* CML B3 and *L. lactis* 43103. All these strains are derived from the wild type strain *L. lactis* NCIMB 702118.

Culture Media:

Shaken flask cultures were carried out in YEC medium, whose composition is as follows: 10 g/L glucose, 5 g/L yeast extract, and 20 mM sodium citrate buffer (pH 7.0).

Fermenter cultures were carried out in a carbohydrate-rich medium. The term "carbohydrate-rich culture medium", as used herein, refers to any culture medium of those known in the art containing energy, carbon and nitrogen sources assimilable by the strain *L. lactis* 43103, and that allows its growth and a high production of either 2,3-BDO, acetoin or lactic acid, depending on culture conditions, by the same. Specifically, the carbohydrate-rich medium used in the examples provided in this invention contains an initial carbohydrate concentration of 100 g/L, in the form of glucose or sucrose, either pure or from beet molasses.

Culture Methods:

The following types of cultures were used throughout this invention:

A. Shaken flask cultures: Aerobic shaken flak cultures were carried out in 100 mL Erlenmeyer flasks containing 20 mL YEC medium, at room temperature and 250 rpm rotary shaking. Cultures were started by inoculating the medium with a 1% (v/v) inoculum, obtained as a pre-culture in YEC medium grown for 24 hours after inoculation with a colony of the strain, grown on a plate of YEC agar medium for 3 days.

B. Fermenter cultures (batch): Fermenter batch cultures were carried out using a laboratory fermenter equipped with a 1 L-reactor and containing 750 mL of a carbohydrate-rich medium. Fermentations were carried out at 30° C. and a stirring rate of 500 or 750 rpm. In aerobic cultures, dissolved oxygen concentration was set between 10 and 30% with respect to medium saturation concentration, by passing through the culture medium an air flow of 1 L/L/min, either alone or oxygen-enriched. In anaerobic cultures, the stirring rate was set at 500 rpm and the air supply was removed. Fermentation pH was set at different values from experiment to experiment, and was maintained through the automatic addition of 5 M NaOH. Fermentations were started by inoculating the medium with 100 mL of a pre-culture in YEC medium grown in a 500 mL Erlenmeyer flask for 24 hours, after inoculation with a 1 mL-cryovial of the strain preserved in 10% glycerol at −80° C.

C. Fermenter cultures (fed-batch): Fermenter fed-batch cultures were carried out as in method B, but including an additional feeding of 100 g/L of glucose when the carbon source approached exhaustion.

Measurement of Metabolite Concentration:

2,3-BDO, acetoin, lactate, acetate, ethanol and glucose or sucrose concentrations in fermentation broth were measured by HPLC using an Aminex HPX-87H 300×7.8 mm (Bio Rad) column and a Microguard Cation H Refill Cartridge precolumn, with the following conditions: mobile phase, 0.01 N $H_2SO_4$; flow rate, 0.7 mL/min; column temperature, 55° C.; detector temperature, 35° C. Peak quantification was done with a refractive index detector.

Bacterial Growth Measurement:

Bacterial growth or biomass concentration in YEC medium was measured as the optical density at 600 nm ($OD_{600}$) of properly diluted cell suspensions. When cultures were carried out in a carbohydrate-rich medium, biomass could not be measured due to the presence in the culture medium of insoluble particles that interfered with measurements.

Example 1

Isolation of the mutant strain *L. lactis* B3

A single colony of the wild type strain *L. lactis* NCIMB 702118 was cultured at 30° C. (250 rpm) in a 100 mL Erlenmeyer flask containing 10 mL of 1% glucose-supplemented M17 medium (Terzaghi B E, Sandine W E, "Improved medium for Lactic Streptococci and their bacteriophages", Appl. Microbiol., 1975, vol. 29, pp. 807-813; composition in g/L: tryptone, 2.5; meat peptone, 2.5; soybean peptone, 5.0; meat extract, 5.0; yeast extract, 2.5; sodium glycerophosphate, 19.0; magnesium sulfate, 0.25; and ascorbic acid, 0.50) for 24 hours. Bacterial cells were washed twice by centrifugation/resuspension in 100 mM potassium phosphate buffer (pH 7.5) and finally resuspended in 1 mL of the same buffer. To this concentrated cell suspension 120 μL of the chemical mutagen ethyl methanesulfonate (EMS) were added, and the resulting suspension was incubated at 25° C. for 15 minutes with gentle shaking. Then, cells were washed twice again with 10 mL of the same potassium phosphate buffer, resuspended in 10 mL of M17 medium with 1% glucose and incubated with shaking for 1 hour.

Finally, appropriate dilutions of the resulting cell suspension were plated on selection medium agar plates. Selection medium was a modified M17 medium containing a lower buffering capacity (only a 5% of that of the standard one) and, in addition, supplemented with 100 mg/L 2,3,5-triphenyl tetrazolium. On this selection medium, while the wild type strain forms pink colonies, low lactic acid producing strains are expected to appear as red/brown colonies.

From a total of 26,000 colonies plated on selection medium four red-coloured colonies were isolated and analyzed for metabolite production (method A). Among these isolated colonies the strain *L. lactis* B3 was finally selected, as it showed the highest 2,3-BDO and the lowest lactic acid production. Growth and metabolite production are shown in table 1.

Example 2

Isolation of the Strain *L. lactis* 43103

Strain *L. lactis* 43103 was obtained using the method of genome shuffling, through fusion of protoplasts of the mutant strains *L. lactis* B4 and B3. From shaken flask cultures in YEC medium of the strains *L. lactis* B4 and B3, grown for 20 hours, 1 mL each was taken separately and centrifuged at 14,000 rpm for 5 min. Cells were washed three times in PM (Protoplasting Medium: 10 mM Tris-HCl (pH 7.0), 20 mM $CaCl_2$ and 0.5 M sucrose) and finally resuspended in 650 μL PM supplemented with 5 mg/mL lysozyme and 100 U/mL mutanolysin. Bacterial suspensions were incubated at 37° C. for 2 hours, with gentle shaking, in order to obtain their respective protoplasts. Protoplasts were washed twice in PM and resuspended in 0.5 mL of the same medium.

A 100 μL sample of the protoplast suspension of the strain *L. lactis* B4 was heated in a water bath at 60° C. for 30 min to inactivate protoplasts. In an 1.5 mL Eppendorf tube, 50 μL each of protoplast suspensions of the strains *L. lactis* B4 (heat inactivated) and B3 (not inactivated) were mixed, and then 900 μL PM supplemented with 50% PEG 6000 was added, gently mixing, and was incubated at 37° C. for 10 min to induce protoplast fusion. Then, suspension was washed twice with PM to stop protoplast fusion process. The whole resulting suspension was used to inoculate a 100 mL Erlenmeyer flask containing 5 mL RM (Regeneration Medium: 1% glucose, 5 g/L yeast extract, 20 mM acid citric (pH 7,0), 25 mM $MgCl_2$, 25 mM $CaCl_2$, 2.5% gelatin, 0.5 M sucrose) and was cultured at room temperature (125 rpm) overnight.

Appropriate dilutions of the above culture were plated on unbuffered YEC medium plates (without citrate) supplemented with 100 mg/L 2,3,5-triphenyl tetrazolium, and were incubated for 48 hours, until colony appearance. A total of 18 colonies showing a distinctive aspect were isolated in a fresh plate of the same medium, and were then analyzed for growth and metabolite production (method A), and compared with strains *L. lactis* B4, B3 and wild type. Among all the isolated strains, one of them, named *L. lactis* 43103, displayed the best features regarding acetoin/2,3-BDO/lactic acid production. Results are shown in table 1.

TABLE 1

Growth and metabolite production (method A) by the wild type and B4, B3 and 43103 mutant strains of *L. lactis* in YEC medium.

| Strain | $DO_{600}$ | Acetoin | 2,3-BDO | Lactate |
|---|---|---|---|---|
| Wild type* | 2.3 | <1.0 | <0.5 | 40.5 |
| B4 | 4.5 | 52.8 | 2.9 | 8.5 |
| B3 | 4.0 | 27.4 | 14.2 | 34.4 |
| 43103 | 4.3 | 44.5 | 11.9 | 6.8 |

Metabolite concentrations are expressed as mM.
*More than 50% of glucose remains unused as a result of the limited buffering of the medium and the large lactic acid production.

Examples 3-6

Aerobic Fermentations of a Beet Molasses Medium by the Strain *L. lactis* 43103 at Different pH Values The strain *L. lactis* 43103 was used to carry out a series of aerobic fermentations of a carbohydrate-rich medium, containing beet molasses as carbon source, at different pH values between 7.0 and 5.5, according to method B described in the General methods section. Dissolved oxygen concentration was set at 30% and stirring rate at 750 rpm. Results of metabolite production are shown in table 2.

TABLE 2

Metabolite production in aerobic fermentations of a beet molasses medium (method B) by the strain *L. lactis* 43103 at different pH values.

| pH | Acetoin | 2,3-BDO | Lactate |
|---|---|---|---|
| 7.0 | 376 | 99 | 90 |
| 6.5 | 365 | 216 | 214 |
| 6.0 | 183 | 378 | 205 |
| 5.5 | 57 | 371 | 75 |

Metabolite concentrations are expressed as mM.

Examples 7-11

Aerobic fermentations of a beet molasses medium by the strain *L. lactis* 43103 at pH 5.5 and different values of dissolved oxygen concentration and stirring rate The strain *L. lactis* 43103 was used to carry out a series of aerobic fermentations of a carbohydrate-rich medium, containing beet molasses as carbon source, at pH 5.5 and different values of dissolved oxygen concentration, between 10 and 30%, and stirring rate, between 500 and 750 rpm, according to method B described in the General methods section.

Results of metabolite production are shown in table 3, where the values previously obtained at 30% dissolved oxygen and 750 rpm are included as reference.

TABLE 3

Metabolite production in aerobic fermentations of a beet molasses medium (method B) by the strain *L. lactis* 43103 at pH 5.5 and different values of dissolved oxygen concentration and stirring rate.

| $DO^1$ | Stir. rate$^2$ | Acetoin | 2,3-BDO | Lactate |
|---|---|---|---|---|
| 30% | 750 | 57 | 371 | 75 |
| 20% | 750 | 43 | 479 | 77 |
| 10% | 750 | 35 | 589 | 132 |
| 30% | 500 | 53 | 436 | 95 |
| 20% | 500 | 57 | 556 | 121 |
| 10% | 500 | 42 | 515 | 113 |

Metabolite concentrations are expressed as mM.
$^1$DO, dissolved oxygen concentration, expressed as the % with respect to medium saturation concentration.
$^2$Stir. rate, stirring rate, expressed as rpm.

Examples 12-14

Aerobic Fermentations of a Medium Containing Different Carbon Sources by the Strain *L. lactis* 43103 at pH 5.5

The strain *L. lactis* 43103 was used to carry out a series of aerobic fermentations of a carbohydrate-rich medium, containing either pure glucose, glucose syrup or pure sucrose as carbon sources, at pH 5.5, 10% dissolved oxygen concentration and 750 rpm stirring rate, according to method B described in the General methods section. Results of metabolite production are shown in table 4.

TABLE 4

Metabolite production in aerobic fermentations of a glucose, glucose syrup or sucrose medium (method B) by the strain *L. lactis* 43103 at pH 5.5.

| Carbon source | Acetoin | 2,3-BDO | Lactate |
|---|---|---|---|
| Glucose | 65 | 491 | 33 |
| Glucose syrup | 14 | 556 | 90 |
| Sucrose | 35 | 578 | 71 |

Metabolite concentrations are expressed as mM.

Example 15

Aerobic Fed-Batch Fermentation of a Medium Containing Glucose by the Strain *L. lactis* 43103 at pH 6.0

The strain *L. lactis* 43103 was used to carry out an aerobic fermentation under fed-batch mode of a carbohydrate-rich medium, containing glucose as carbon source, at pH 6.0, 10% dissolved oxygen concentration and 750 rpm stirring rate, according to method C described in the General methods section. Results of metabolite production are shown in table 5.

TABLE 5

Metabolite production in an aerobic fed-batch fermentation of a
glucose medium (method C) by the strain *L. lactis* 43103 at pH 6.0.

| Carbon source | Acetoin | 2,3-BDO | Lactate |
|---|---|---|---|
| Glucose | 40 | 851 | 47 |

Metabolite concentrations are expressed as mM.

Example 16

Anaerobic Fermentation of a Beet Molasses Medium by the Strain *L. lactis* 43103

The strain *L. lactis* 43103 was used to carry out an anaerobic fermentation of a carbohydrate-rich medium, containing beet molasses as carbon source, according to method B described in the General methods section. Results of metabolite production are shown in table 5.

TABLE 6

Metabolite production in an anaerobic fermentation of a beet
molasses medium (method B) by the strain *L. lactis* 43103.

| Oxygen | Acetoin | 2,3-BDO | Lactate |
|---|---|---|---|
| Anaerobiosis | 7 | 79 | 975 |

Metabolite concentrations are expressed as mM.

REFERENCES CITED IN THE APPLICATION

Hässler, T., et al. "Enhanced fed-batch fermentation of 2,3-butanediol by *Paenibacillus polymyxa* DSM 365" Bioresource technology 2012 vol. 124, pp. 237-244

Ge, Y., et al. "Contracted but effective: production of enantiopure 2,3-butanediol by thermophilic and GRAS *Bacillus licheniformis*". Green Chemistry, 2016

Nielsen, D. R., et al. "Metabolic Engineering of Acetoin and meso-2,3-Butanediol Biosynthesis in *E. coli.*", Biotechnol. J. 2010, vol. 5, pp. 274-284

Lian, J., et al. "Metabolic engineering of a *Saccharomyces cerevisiae* strain capable of simultaneously utilizing glucose and galactose to produce enantiopure (2R, 3R)-butanediol" Metabolic engineering 2014, vol. 23, pp. 92-99

Platteeuw C, et al. "Metabolic engineering of *Lactococcus lactis*—influence of the overproduction of alpha-acetolactate synthase in strains deficient in lactate-dehydrogenase as a function of culture conditions", Appl. Environ. Microbiol. 1995, vol. 61, pp. 3967-71

Gaspar P, et al. "High yields of 2,3-butanediol and mannitol in *Lactococcus lactis* through engineering of NAD(+) cofactor recycling", Appl. Environ. Microbiol. 2011, vol. 77, pp. 6826-35

Liu J, et al. "Combining metabolic engineering and biocompatible chemistry for high-yield production of homo-diacetyl and homo-(S,S)-2,3-butanediol", Metabolic engineering 2016, vol. 36, pp. 57-67

PCT/US2009/058834

Zhang Y X, et al. "Genome shuffling leads to rapid phenotypic improvement in bacteria", Nature 2002, vol. 415, pp. 644-646

FR2777905

ES2352633B1

Terzaghi B E, Sandine W E, "Improved medium for Lactic Streptococci and their bacteriophages", Appl. Microbiol., 1975, vol. 29, pp. 807-813

CLAUSES

1. A method to produce a modified strain of the bacterium *Lactococcus lactis* that comprises a step of fusion of two protoplasts from two *Lactococcus lactis* parental strains which, compared to a wild type strain of *Lactococcus lactis*, show: (a) an increased ability to produce acetoin and/or 2,3-butanediol, and (b) a decreased ability to produce lactic acid, when cultured under aerobic conditions.

2. The method according to claim 1, wherein each of the *Lactococcus lactis* parental strains is obtained by subjecting a wild type strain of *Lactococcus lactis* to a mutagenesis treatment.

3. The method according to claim 2, wherein the mutagenesis treatment is carried out using ethyl methanesulfonate (EMS).

4. The method according to any one of claims 1 to 3, wherein one of the *Lactococcus lactis* parental strains has an increased ability to produce acetoin and the other one has an increased ability to produce 2,3-butanediol, compared to a wild type strain of *Lactococcus lactis*, when cultured under aerobic conditions.

5. The method according to any one of claims 1 to 4, wherein one of the two *Lactococcus lactis* parental strains subjected to the protoplast fusion step is the strain *Lactococcus lactis* CML B4, deposited at the Spanish Type Culture Collection under accession number CECT 7512, wherein this strain has an increased ability to produce acetoin and a decreased ability to produce lactic acid, compared to a wild type strain of *Lactococcus lactis*, when cultured under aerobic conditions.

6. The method according to any one of claims 1 to 5, wherein one of the two *Lactococcus lactis* parental strains subjected to the protoplast fusion step is the strain *Lactococcus lactis* CML B3, wherein this strain has an increased ability to produce 2,3-butanediol and acetoin and a decreased ability to produce lactic acid, compared to a wild type strain of *Lactococcus lactis*, when cultured under aerobic conditions.

7. A modified strain of the bacterium *Lactococcus lactis* obtainable by the method described in any one of claims 1 to 6.

8. The modified strain of the bacterium *Lactococcus lactis* according to claim 7 and deposited at the Spanish Type Culture Collection under accession number CECT 9139.

9. A method of production of 2,3-butanediol that comprises the aerobic fermentation of a carbohydrate-rich culture medium by a bacterial strain as defined in any one of claims 7 to 8.

10. The method of 2,3-butanediol production according to claim 9, comprising the following steps:
(a) Pre-culture of a strain as defined in any one of claims 7 to 8;
(b) Inoculation of a carbohydrate-rich culture medium with the pre-culture obtained in step (a);
(c) Fermentation of carbohydrates present in the culture medium inoculated in step (b) at 20-40° C.; pH 5.5-6.0 and 5-100% dissolved oxygen concentration; and
(d) Separation of cells from the fermented broth resulting from step (c).

11. The method of 2,3-butanediol production according to claim 10, additionally comprising a step of purification of the 2,3-butanediol present in the cell-free fermentation broth resulting from step (d).

12. A method of production of acetoin, that comprises the aerobic fermentation of a carbohydrate-rich culture medium by a bacterial strain as defined in any one of claims 7 to 8.

13. The method of acetoin production according to claim 12, comprising the following steps:
(a) Pre-culture of a strain as defined in any one of claims 7 to 8;
(b) Inoculation of a carbohydrate-rich culture medium with the pre-culture obtained in step (a);
(c) Fermentation of carbohydrates present in the culture medium inoculated in step (b) at 20-40° C.; pH 6.5-7.5 and 30-100% dissolved oxygen concentration; and
(d) Separation of cells from the fermented broth resulting from step (c).

14. The method of acetoin production according to claim 13, additionally comprising a step of purification of the acetoin present in the cell-free fermentation broth resulting from step (d).

15. A method of production of lactic acid that comprises the anaerobic fermentation of a carbohydrate-rich culture medium by a bacterial strain as defined in any one of claims 7 to 8.

The invention claimed is:

1. A *Lactococcus lactis* strain 43103 deposited at the Spanish Type Culture Collection under accession number CECT 9139, wherein said strain has an increased ability to produce acetoin and 2,3-butanediol and a decreased ability to produce lactic add when cultured under aerobic conditions.

2. A method of production of 2,3-butanediol that comprises the aerobic fermentation of a carbohydrate-containing culture medium by the bacterial strain as defined in claim 1.

3. The method of 2,3-butanediol production according to claim 2, comprising the following steps: (a) Pre-culture of the *Lactococcus lactis* strain 43103 deposited at the Spanish Type Culture Collection under accession number CECT 9139; (b) Inoculation of a carbohydrate-containing culture medium with the pre-culture obtained in step (a); (c) Fermentation of carbohydrates present in the culture medium inoculated in step (b) at 20-40° C.; pH 5.5-6.0 and 5-100% dissolved oxygen concentration; and (d) Separation of cells from the fermented broth resulting from step (c).

4. The method of 2,3-butanediol production according to claim 3, further comprising a step of purification of the 2,3-butanediol present in the cell-free fermentation broth resulting from step (d).

5. A method of production of acetoin, that comprises the aerobic fermentation of a carbohydrate-containing culture medium by the bacterial strain as defined in claim 1.

6. The method of acetoin production according to claim 5, comprising the following steps: (a) Pre-culture of the *Lactococcus lactis* strain 43103 strain deposited at the Spanish Type Culture Collection under accession number CECT 9139; (b) Inoculation of a carbohydrate-containing culture medium with the pre-culture obtained in step (a); (c) Fermentation of carbohydrates present in the culture medium inoculated in step (b) at 20-40° C.; pH 6.5-7.5 and 30-100% dissolved oxygen concentration; and (d) Separation of cells from the fermented broth resulting from step (c).

7. The method of acetoin production according to claim 6, further comprising a step of purification of the acetoin present in the cell-free fermentation broth resulting from step (d).

8. A method of production of lactic add that comprises the anaerobic fermentation of a carbohydrate-containing culture medium by the bacterial strain as defined in claim 1.

* * * * *